United States Patent [19]

Foery et al.

[11] 4,004,909
[45] Jan. 25, 1977

[54] BETA-HALOGENOETHYL-SILANES AS FRUIT ABSCISSION, RIPENING AND THINNING AGENTS

[75] Inventors: Werner Foery, Basel; Hans Peter Fischer, Bottmingen, both of Switzerland

[73] Assignee: Ciba-Geigy Corporation, Ardsley, N.Y.

[22] Filed: July 14, 1975

[21] Appl. No.: 595,812

Related U.S. Application Data

[60] Division of Ser. No. 443,179, Feb. 15, 1974, Pat. No. 3,912,493, which is a continuation-in-part of Ser. No. 186,392, Oct. 4, 1971, abandoned.

[52] U.S. Cl. .......................... 71/79; 71/77
[51] Int. Cl.² ............................ A01N 9/00
[58] Field of Search ........................ 71/79, 86

[56] References Cited

UNITED STATES PATENTS

| | | | |
|---|---|---|---|
| 3,183,076 | 5/1967 | Leasure et al. | 71/79 |
| 3,390,976 | 7/1968 | Leasure et al. | 71/79 |
| 3,421,881 | 1/1969 | Leasure et al. | 71/79 |
| 3,879,188 | 4/1975 | Fritz et al. | 71/86 |

OTHER PUBLICATIONS

Boye et al. I, "Studies in Silico–Organic Cmpds. etc.," (1950), J. Org. Chem. 16, pp. 391–394 (1951).
Boye et al. II, "Studies in Silico–Organic Cmpds. etc.," (1952), J. Org. Chem. 17, pp. 1386–1392 (1952).

*Primary Examiner*—Glennon H. Hollrah
*Attorney, Agent, or Firm*—Harry Falber

[57] ABSTRACT

The present invention relates to methods for the regulation of plant growth, especially for fruit abscission, acceleration of ripening and latex discharge. The active substances used in these methods correspond to the formula

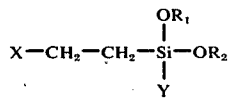

wherein X is chlorine or bromine, Y represents chlorine and $R_1$ and $R_2$ are both methyl, or the radical $-OR_3$ and each of the radicals $R_1$, $R_2$ and $R_3$ independently represent alkyl radicals, or the group $-COR_4$, wherein $R_4$ stands for an alkyl radical.

6 Claims, No Drawings

BETA-HALOGENOETHYL-SILANES AS FRUIT ABSCISSION, RIPENING AND THINNING AGENTS

RELATED APPLICATION

This is a divisional of application Ser. No. 443,179, filed Feb. 15, 1974, now U.S. Pat. No. 3,912,493, which, in turn, is a continuation-in-part of application Ser. No. 186,392, filed Oct. 4, 1971, now abandoned.

The present invention relates to new processes for the regulation of plant growth by the use of β-halogen-ethyl-silanes as active substances.

The β-halogen-ethyl-silanes contained as active substances correspond to formula I:

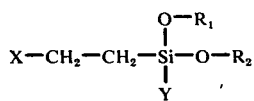

$$X-CH_2-CH_2-Si(O-R_1)(O-R_2)Y \quad (I)$$

wherein X represents chlorine or bromine, Y represents chlorine or the radical $-OR_3$; $R_1$, $R_2$ and $R_3$ represent, independently of each other, alkyl radicals or the group $-CO-R_4$ wherein $R_4$ stands for an alkyl or halogenalkyl radical.

By alkyl radicals in formula I are meant straight-chain or branched radicals having 1 to 5 carbon atoms, such as, e.g. methyl, ethyl, n-propyl, isopropyl, n-butyl, or sec-butyl.

The β-halogen-ethyl-silanes of formula I affect in a varying manner the growth of parts of plants situated above and below the ground; they are not phytotoxic in the usual concentrations in which they are applied, and have a low toxicity towards warm-blooded animals. The active substances produce no morphological changes or damage which would result in a withering of the plant. The compounds are not mutagenic. Their action differs from that of a herbicidal active substance and of a fertiliser. The action corresponds more to the effects which can be observed on application of ethylene to various parts of plants. It is known that also the plant itself produces, in various stages of development, ethylene to a varying extent, particularly before and during the ripening process of the fruits, and at the end of the vegetation period as the abscission of the fruit and leaves occurs. Since the regulation of ripening and of fruit and leaf abscission by chemical substances is of the greatest commerical significance for the cultivation of fruit, citrus fruits, pineapples and cotton, compounds have been sought with which such effects might be obtained without damage being caused to the treated plants. Various classes of substances have thus meanwhile become known with which it was possible for certain of these effects, with regard to growth regulation, to be achieved; the sphere of action of these substances in no way corresponds, however, to that of ethylene.

Compounds which, under certain conditions, release ethylene are known. Such compounds are relatively unstable under the effects of weather, because they are very susceptible to hydrolysis; or they are phytotoxic. β-Halogen-ethyl-phosphonic acid derivatives are described in the South African Pat. No. 68.1036 as active substances regulating plant growth. These compounds decompose in and on the plant with the release of ethylene, and are therefore similar in action and range of action to ethylene. By virtue of their very low stability, phosphonic acid derivatives are not able, however, to satisfy the demands made on them. As they are stable only in an acid medium, more precisely in a pH-range below 5, the active substance concentrates have to be stabilised by the addition of acids. This acid addition limits, however, the range of application of these active substances with regard to phytotoxic effects. Furthermore, the storage of such sensitive active substance concentrates presents difficulties.

Also, known, as herbicidal active substances, are halogenalkyl-methyl-silanes, cp. U.S. Pat. Nos. 3,390,976 and 3,390,977 and J. K. Leasure et al., J. Med. Chem. 9, 949 (1966). β-Chloroethyl-tris-(alkoxy)-silanes and β-chloroethyl-acetoxy-dialkoxy silanes and β-chloroethyl-diacetoxy-alkoxy silanes have been produced by F. W. Boye et al., J. Org. Chem 16, 391 (1951), resp. 17, 1386 (1952).

The U.S. Pat. No. 3,183,076 describes α-chloroethyl-methyldialkoxy-silanes, which can be used for the promotion of germination power, leaf absicission, etc.

The present invention relates to agents containing, as active substances, β-halogen-ethyl-silanes, the said agents having a stimulating or retarding effect on plant growth in the various stages of developement of the plants. By virtue of the very good stability of the active substances of formula I, these agents must not contain, apart from the usual carriers, distributing agents, and stabilisers protecting against the effects of light and oxidation, any additional acid stabilising additive, and have therefore, an unlimited field of application. The vegetative plant growth and the germination power are influenced by the agents; and the blossom formation, the development of the fruit and the formation of separating tissues promoted. In the case of monocotyledons, an increase in tillering and branching was observed with a simultaneous reduction of growth in height. There was moreover a strengthing of the support tissues of the stalks in the case of the treated plants. The formation of undesirable side shoots is very greatly reduced on various types of plants. Furthermore, gum trees are stimulated to produce a greater latex discharge, an effect which is of great commercial importance. Tests have shown that the rooting of seedlings and cuttings, as well as the developement of tubers in the case of potatoes, is promoted. In addition, there occurs a simultaneous aprouting of dormant rhizomes, which is particularly important in the case of various perennial weeds such as couchgrass, Johnson grass and cyperus, which can then be easily destroyed or suppressed by herbicides. The germination capacity of seeds such as, e.g. seed potatoes and legumes is promoted with low concentrations, and prevented with higher conentrations. Both these effects are commercially important. A control of the blossoming time and of the number of blossoms is possible in the case of many ornamental and cultivated plants. This effect is an especially important factor in connection with pineapples. If all the trees or shrubs blossom simultaneously, then the crops can be gathered within a comparatively short space of time. With regard to cucurbitaceae, there ocurs a displacement of the blossom sex differentiation in favour of pisstillate flowers.

The active substances promote the development of abscission layers, particularly between stalks and petioles. Consequently, fruits of all kinds, e.g. apples, pears, peaches, tomatoes, bananas, prunes, pineapples, cherries, citrus fruits and, particularly oil fruits (olives) can be separated from the fruit stems manually or mechanically without the exertion of great force. Damage to foliage and branches, which results from shaking tress and shrubs or by plucking fruit, is largely avoided and production capacity increased. Tests have also shown that in the case of fruit trees, particularly peaches, there occurs a thinning of blossom and fruit.

The extent and the nature of the action are dependent on the most diverse factors, particularly on the time of application with regard to the stage of development of the plant, and on the application concentration. These factors vary, however, depending on the type of plant and on the desired effect. Thus, for example, plants of which the fruit is to be sold, or in some other way utilised, will be treated after blossoming or at an appropriate interval of time before the gathering of the crop. Application of the active substances is effected by the use of solid or liquid agents, these being applied to parts of plants above the ground, to the surface of the soil, as well as into the soil itself. The preferred method is the application to the parts of plants above the soil, for which purpose solutions or aqueous suspensions are most suitable. In addition to solutions and dispersions for the treatment of the growth substrate (soil), dusts, granulates and scattering agents are also suitable.

The plant growth regulating action of the active substances can often be positively influenced by the addition of organic or inorganic acids and bases (e.g. acetic acid or sodium carbonate.)

The beta-halogen-ethyl silanes are generally produced by reaction of a beta-halogen-ethyl-trichlorsilane of formula II

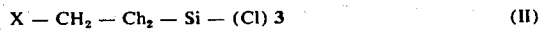

$$X - CH_2 - Ch_2 - Si - (Cl)_3 \quad (II)$$

with three equivalents of an acid of formula III:

$$R_4 - \underset{\underset{O}{\|}}{C} - OH \quad (III)$$

or of a carboxylic acid anhydride of formula IV:

$$R_4 - \underset{\underset{O}{\|}}{C} - O - \underset{\underset{O}{\|}}{C} - R_4 \quad (IV)$$

to give a compound of formula V:

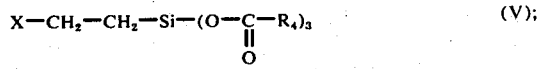

$$X - CH_2 - CH_2 - Si - (O - \underset{\underset{O}{\|}}{C} - R_4)_3 \quad (V);$$

and, optionally, by stepwise exchange of two or three of the radicals

$$-O - \underset{\underset{O}{\|}}{C} - R_4$$

by radicals of alcohols of the formulae VI, VII, VIII

$$R_1OH \quad (VI)$$
$$R_2OH \quad (VII)$$
$$R_3OH \quad (VIII)$$

If, in the starting compound of formula II X represents bromine, also low molecular alkanols may be used for the exchange of the radicals —O—CO—R$_4$ in formula V.

X in formula II represents chlorine or bromine; R$_4$ in formulae III and IV has the meaning given under formula I; and R$_1$, and R$_2$ and R$_3$ in formulae VI, VII and VIII have the meaning given under formula I.

As in the reaction according to the invention, the exchange of the 3 chlorine atoms of the starting compound of formula III occurs stepwise, it is clear that intermediates, i.e. dichloro- and monochloro-silanes of formulae

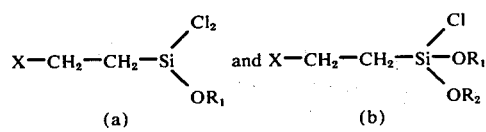

$$X-CH_2-CH_2-Si\diagup^{Cl_2}_{\diagdown OR_1} \quad \text{and} \quad X-CH_2-CH_2-Si\diagup^{Cl}_{\diagdown OR_2}-OR_1$$
$$\text{(a)} \qquad\qquad\qquad\qquad \text{(b)}$$

can be isolated during the synthesis or as impureties from the crude final product.

The process is preferably carried out in the presence of solvents and/or diluents which are inert to the reactants. Aprotic solvents are particularly suitable, such as, e.g. aliphatic and aromatic hydrocarbons, e.g. hexane, cyclohexane, benzene, toluene, xylene, halogenated hydrocarbons such as chlorinated ethylene, carbon tetrachloride, chloroform, chlorobenzene, also ethers and ethereal compounds such as diethyl ether, tetrahydrofuran, etc..

To obtain a complete reaction, it is also possible for the alcohols, carboxylic acids and carboxylic acid anhydrides employed as reactants to serve, when used in excess, as solvents or diluents.

Furthermore, it can be necessary in some cases to add an acid-binding agent to the reaction mixture. Suitable for this purpose are, in particular, tertiary amines such as trialkylamines, e.g. triethylamine, pyridine and pyridine bases, dialkylanilines, etc..

The reaction temperatures are in the range of 0° to 100° C; the reaction duration can be between a few minutes and several days, and depends to a great extent on the reactivity of the alcohols employed.

Compositions according to the invention are produced in a manner known per se by the intimate mixing and grinding of active substances of the general formula I with suitable carriers optionally with the addition of dispersing agents or solvents which are inert to the active substances.

Water-dispersible concentrates of active substance, i.e. wettable powders, pastes and emulsion concentrates, are active substance concentrates which can be diluted with water to obtain any desired concentration. They consist of active substance, carrier, optionally additives which stabilise the active substance, surface-active substances, and anti-foam agents and, optionally, solvents. The concentration of active substance in these agents is 0.5 – 80%.

The wettable powders and pastes are obtained by the mixing and grinding of the active substances with dispersing agents and pulverulent carriers, in suitable devices, until homogeneity is attained. Suitable carriers are, e.g. the following: kaolin, talcum, bole, loess, chalk, limestone, ground limestone, attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, celluslose powder, residues of plant extractions, active charcoal, etc., alone or in admixture with each other.

Suitable dispersing agents are, e.g. the following: condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalene-sulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkalimetal and alkaline-earth metal salts.

To these mixtures may also be added additives stabilising the active substance, and/or non-ionic, anionactive and cation-active substances, which, for example, improve the adhesiveness of the active substances on plants and on parts of plants (adhesives and agglutinants), and/or ensure a better wettability (wetting agents). Suitable adhesives are, for example, the following: olein/lime mixture, cellulose derivatives (methyl cellulsoe, carboxymethyl celluslose), hydroxyethylene glycol ethers of mono-and dialkylphenols having 5 – 15 ethylene oxide radicals per molecule and 8 – 9 carbon atoms in the alkyl radical, ligninsulphonic acid, alkali metal and alkaline-earth metal salts thereof, polyethylene glycol ethers (carbowaxes), fatty alcohol polyglycol ethers having 5 – 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea-formaldehyde, as well as latex products. The active substances are so mixed, ground, sieved and strained with the above-mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g. the following: ketones, benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances) of the general formula I is (or are) dissolved in suitable organic solvents, solvent mixtures, or water. The following can be used as organic solvents: aliphatic and aromatic hydrocarbons, chlorinated derivatives thereof, alkylnaphthalenes, or mineral oils on their own or in admixture with each other. The solutions should contain the active substances in a concentration range of from 1 to 20%.

The solid preparations, such as dusts, scattering agents and granulates, contain solid carriers such as those mentioned in the foregoing, and, optionally, additives stabilising the active substance. The particle size of the carriers is for dusts advantageously up to about 0.1 mm; for scattering agents from about 0.075 mm to 0.2 mm; and for granulates 0.2 mm or coarser. The concentrations of active substance in the solid preparations are from 0.5 to 80%.

All the mentioned active substance concentrates may also contain agents stabilising against the effects of light, and antioxidants.

Granulate

The following substances are used for the preparation of a 5% granulate:
  5 parts of 2-chloroethyl-tris-(ethoxy)-silane,
  0.25 parts of epichlorhydrin,
  0.25 parts of cetyl polyglycol ether,
  3.50 parts of polyethylene glycol ("carbowax"),
  91 parts of kaolin (particle size 0.2 — 0.8 mm).

The active substance is mixed with epichlorohydrin and the mixture dissolved in six parts of acetone; to the solution are then added polyethylene glycol and cetyl polyglycol ether. The thus obtained solution is sprayed on to kaolin, and the acetone subsequently evaporated in vacuo.

Wettable powder

The following constituents are used for the preparation of (a) a 40%, (b) a 50%, (c) a 25%, and (d) a 10% wettable powder:

a.

40 parts of 2-chlorethyl-tris-(ethxoy)-silane,
  5 parts of sodium lignin sulphonate,
  1 part of sodium dibutyl-naphthalene sulphonate,
  54 parts of silicic acid;

b.

50 parts of 2-chloroethyl-tris-(ethoxy)-silane,
  5 parts of alkylaryl sulphonate ("Tinovetin B"),
  10 parts of calcium lignin sulphonte,
  1 part of Champagne chalk/hydroxyethyl cellulose mixture (1 : 1),
  20 parts of silicic acid,
  14 parts of kaolin;

c.

25 parts of 2-chloroethyl-tris-(ethoxy)-silane,
  5 parts of the sodium salt of oleylemthyl tauride,
  2.5 parts of naphthalenesulphonic acid/formaldehyde condensate,
  0.5 parts of carboxymethyl cellulose,
  5 parts of neutral potassium aluminium silicate,
  62 parts of kaolin;

d.

10 parts of 2-chloroethyl-tris-(ethoxy)-silane,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives; the mixture is subsequently ground in suitable mills and rollers. Wettable powders are thus obtained which can be diluted with water to give suspensions of any desired concentration. Such suspensions are employed, e.g. for the removal of undesired side shoots, for the tillering of lawns, and for the rooting of seedlings and cuttings, etc..

Emulsion concentrate

The following constituents are mixed together to produce 25% emulsion concentrates:

a.

25 parts of 2-chlorethyl-tris-(ethoxy)-silane,
5 parts of a mixture of nonylphenolpolyoxyethylene and calcium-dodecylbenzene sulphonate,
70 parts of sylene;

b.

25 parts of 2-chloroethyl-tris-(ethoxy)-silane,
10 parts of a mixture of nonylphenolpolyoxyethylene and calcium-dodecylbenzene sulphonate,
65 parts of cyclohexanone.

This concentrate can be diluted with water to obtain emulsions of any desired concentration. Such emulsions are suitable for the thinning out of blossom and fruit, for the accelerated ripening of fruits, and for the promotion of fruit abscission. Compounds of the formula $$X-CH_2-CH_2-Si(OR_1)(OR_2)(OR_3)$$

| | $R_1$ | $R_2$ | $R_3$ | X | physical data bp. °C/Torr |
|---|---|---|---|---|---|
| 1 | $CH_3$ | $CH_3$ | $CH_3$ | Cl | 113–114°/106 |
| 2 | $C_2H_5$ | $C_2H_5$ | $C_2H_5$ | Cl | 90°/9 |
| 3 | $C_2H_5$ | $C_2H_5$ | $C_2H_5$ | Br | 80–81°/14 |
| 4 | iso-$C_3H_7$ | i-$C_3H_7$ | i-$C_3H_7$ | Cl | 85–86°/4 |
| 5 | n-$C_4H_9$ | n-$C_4H_9$ | n-$C_4H_9$ | Cl | 138°/4 |
| 6 | (2-$CH_3$)$C_4H_8$ | (2-$CH_3$)$C_4H_8$ | (2-$CH_3$)$C_4H_8$ | Cl | 115–118°/0.2 |
| 7 | (3-$CH_3$)$C_4H_8$ | (3-$CH_3$)$C_4H_8$ | (3-$CH_3$)$C_4H_8$ | Cl | 96–100°/0.1 |
| 8 | n-$C_3H_7$ | n-$C_3H_7$ | n-$C_3H_7$ | Cl | 107–108°/4 |
| 9 | sec-$C_4H_9$ | sec-$C_4H_9$ | sec-$C_4H_9$ | Cl | 117–118°/4 |
| 10 | iso-$C_4H_9$ | iso-$C_4H_9$ | iso-$C_4H_9$ | Cl | 122–123°/4 |
| 11 | n-$C_5H_{11}$ | n-$C_5H_{11}$ | n-$C_5H_{11}$ | Cl | 164–166°/4 |
| 12 | $CH_3$ | $CH_3$ | n-$C_3H_7$ | Cl | 102°/18 |
| 13 | $CH_3$ | $CH_3$ | n-$C_4H_9$ | Cl | 103–105°/10 |
| 14 | $CH_3$ | $CH_3$ | n-$C_5H_{11}$ | Cl | 129°/21 |
| 15 | $C_2H_5$ | $C_2H_5$ | n-$C_4H_9$ | Cl | 116°/11 |
| 16 | n-$C_3H_7$ | n-$C_3H_7$ | $CH_3$ | Cl | 121°/18 |
| 17 | n-$C_4H_9$ | n-$C_4H_9$ | $CH_3$ | Cl | 130–132°/10 |
| 18 | n-$C_4H_9$ | n-$C_4H_9$ | $C_2H_5$ | Cl | 137°/11 |

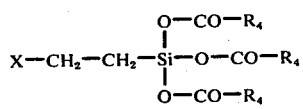

| | $R_4$ | X | physical data bp. °C/Torr |
|---|---|---|---|
| 19 | $CH_3$ | Cl | 85–88°/0.1 |
| 20 | $C_2H_5$ | Cl | 102–104°/0.05 |
| 21 | $CH_3$ | Br | 120–122°/0.06 |
| 22 | $C_2H_5$ | Br | 115–125°/0.002 |
| 23 | n-$C_5H_{11}$ | Cl | $n_D^{20} = 1.4286$ |

$$X-CH_2-CH_2-Si(OR_1)(OR_2)(O-CO-R_4)$$

| | $R_1$ | $R_2$ | $R_4$ | X | physical data bp. °C/Torr |
|---|---|---|---|---|---|
| 24 | $C_2H_5$ | $C_2H_5$ | $CH_3$ | Cl | 117°/20 |
| 25 | n-$C_3H_7$ | n-$C_3H_7$ | $CH_3$ | Cl | 122°/6,5 |
| 26 | n-$C_4H_9$ | n-$C_4H_9$ | $CH_3$ | Cl | 144°/8 |
| 27 | n-$C_5H_{11}$ | n-$C_5H_{11}$ | $CH_3$ | Cl | 155°/5 |
| 28 | $CH_3$ | $CH_3$ | $C_2H_5$ | Cl | 98–99°/7 |
| 29 | n-$C_3H_7$ | n-$C_3H_7$ | $C_2H_5$ | Cl | 139/10 |
| 30 | n-$C_5H_{11}$ | n-$C_5H_{11}$ | $CH_3$ | Br | 104–110°/0.001 |

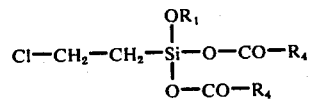

| | $R_1$ | $R_4$ | physical data bp. °C/Torr |
|---|---|---|---|
| 31 | $CH_3$ | $CH_3$ | 114–115°/8 |
| 32 | $C_2H_5$ | $CH_3$ | 119–120°/8 |
| 33 | n-$C_3H_7$ | $CH_3$ | 115°/3 |

| 34 | 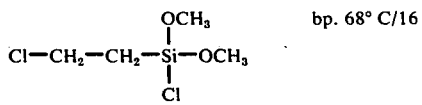 | bp. 68° C/16 |

Performance Characteristics

The active substances of this invention were subjected to a variety of performance determinations. Performance characteristics of controls and the following Leasure et al. prior art compounds were also determined A — bromomethyl-dimethoxy-methyl silane
B — chloromethyl-dimethoxy-methyl silane
C — chloromethyl-diethoxy-methyl silane
D — chloromethyl-diisopropoxy-methyl silane
E — α-chloroethyl-dimethoxy-methyl silane a. Test on olives

On olive trees of the variety "CORATINA" a number of branches were sprayed, about 1 week before their expected harvest, with aqueous compositions of the listed active ingredients. The concentration of the active ingredients in the spray liquid was always 2000 ppm and each treatment was repeated twice. On each tree, some branches were not treated and served as control branches. The tests were evaluated 4 days after spraying by shaking the treated and untreated branches by hand. The olives which fell were counted as percent of the initial number of olives on the corresponding branches, and the results are given in the following table:

| active ingredient 2000 ppm | olive-fall % |
|---|---|
| 1 | 55% |
| 2 | 40% |
| A | 2% |
| B | 2% |
| C | 3% |
| D | 5% |
| E | 10% |
| control (untreated) | 2% | b. Olives

The procedure described in Test (a) hereinabove was repeated on the "Hojiblanca" variety of olive by spraying various concentrations of active substance on to the branches 14 days prior to expected harvest. Olive fall was determined 14 days after application.

| Active Substance | Concentration (ppm) | Olive Fall (%) |
|---|---|---|
| Control | — | 15 |
| 2 | 1000 | 78 |
| 2 | 2000 | 81 |
| 20 | 2000 | 58 |
| 20 | 4000 | 88 |
| 23 | 2000 | 80 |
| 23 | 4000 | 67 |
| 24 | 2000 | 83 |
| 24 | 4000 | 100 | c. Apple Abscission

Apple trees of the variety "Goldent Delicious" were sprayed, 10 days before their expected harvest, with aqueous compositions containing 4000 ppm of the listed active ingredients. Three trees were not treated and served as control. Twelve days after the treatment evaluation of the test was made, by determining, on the basis of 20 apples, the average pull force per apple. The average pull force for the untreated control trees (average value of 20 apples) was 31.2 kg. per apple. The following table indicates the pull force reduction-in percent-of this value.

| active ingredient 4000 ppm | reduction of average abscission force in % |
|---|---|
| 1 | 28% |
| 2 | 21% |
| 4 | 19% |
| B | 4% |
| C | 0% |
| D | |
| control | 0% | d. Apple and Peach Thinning

Apple trees of the variety "Golden Delicious" and peach trees of the variety "Early Golden" were sprayed, subsequent to blossom fall, with aqueous compositions of varying concentrations of active substance. Several trees were retained as controls. At the time of application, the young fruit was counted. Two months later, count was taken of the remaining fruit. These results appear in the following table.

| Active Substance | Concentration (ppm) | Remaining Fruit (%) Apples | Peaches |
|---|---|---|---|
| Control | — | 72 | 52 |
| 19 | 250 | 66 | 36 |
|  | 500 | 62 | 41 |
|  | 1000 | 35 | 26 |

In addition, the fruit on the treated trees was large and readily marketable in contrast to the fruit on the untreated trees which was thin and unpalatable.

e. Orange Abscission

It was determined in the case of citrus fruits — oranges — that the abscission of fruit is appreciable easier after application of the active substances of formula I. Various active substances were sprayed, in the form of solutions in concentrations of 0.2% – 0.4%, on to branches, well hung with fruit, of various orange trees. The tests were evaluated after 14 days according to the method developed by W. C. Wilson and C. H. Hendershott, cp. Proc. Am. Soc. Hort. Sc. 90, 123–129 (1967). The test consists of measuring the force in kg required for the abscission of the fruit.

| Active substance: | Concentration | Force in kg |
|---|---|---|
| 2-chloroethyl-tris-(ethoxy)-silane | 0.2% | 4.5 |
| | 0.4% | 1.5 |

Furthermore, three different crops of navel oranges were tested by spraying, 1 week prior to anticipated ripening, branches well hung with fruit, with solutions in concentrations of 1000, 2000 and 4000 ppm of active substance, respectively. Various branches were retained as controls. The tests were evaluated 1 week after application by measuring the force in kg required for the abscission of the fruit, these results appearing in the following table.

| Active Substance | Concentration (ppm) | Crop 1 Force(kg) | Crop 2 Force(kg) | Crop 3 Force(kg) |
|---|---|---|---|---|
| Control | — | 10.2 | 10.19 | 10.35 |
| 1 | 1000 | — | — | 9.09 |
| 1 | 2000 | — | — | 8.44 |
| 2 | 1000 | 2.5 | — | — |
| 2 | 2000 | 0.8 | 9.76 | — |
| 2 | 4000 | — | 5.57 | — |
| 4 | 2000 | — | — | 7.42 |
| 19 | 2000 | 6.3 | — | — |
| 19 | 4000 | 6.1 | — | — |
| 20 | 2000 | — | 9.13 | — |
| 20 | 4000 | — | 5.72 | — | f. Tomato Ripening

Fully grown but still green tomatoes of the "Selma" variety were plucked and dipped for a period of 60 seconds in an aqueous bath containing 3000 ppm of active substance. Twenty tomatoes were included in a test batch. The control tomatoes were contacted only with water. Six days after dipping, the tomatoes were observed in order to determine the number that had reached full ripeness (red). These results are presented in the following table.

| Active Substance | % Ripe Tomatoes |
|---|---|
| Control | 25 |
| E | 40 |
| 1 | 50 |
| 2 | 50 |
| 4 | 80 | g. Latex Discharge

Caoutchouc rubber trees were fitted with tapping tappin system. A 10% active substance solution in palm oil was then applied to a 5 centimeter wide band of cut bark beneath the tapping cut. Each test sample and control contained 10 trees. Thereafter for a period of 2 months, the exuded latex was tapped every second day. The total amount of recovered latex is noted in the following table.

| Active Substance | Recovered Latex (grams/tree) | Dry Rubber Recovered Above Control (grams/tree) |
|---|---|---|
| Control | 2311.2 | 0 |
| 1 | 4099.0 | 558.3 |
| 2 | 4874.3 | 831.2 |
| 4 | 4127.3 | 574.3 |
| 5 | 4173.6 | 493.3 |
| 34 | 6259.0 | 1198.2 | h. Latex Discharge

Segments of the bark were cut out from the boughs of 12 year old damson trees (*Prunus domestica*). A 10% active substance solution (10 parts active substance, 20 parts xylene, 70 parts castor oil) was then applied to the undamaged surface of the boughs just above and below the above-mentioned incisions, each treatment being repeated on 4 different trees.

4 weeks after said treatment the exuded resin is removed and weighed. The following table gives the average weight of collected resin per treated bough in grams.

| Active substance | Grams resin |
|---|---|
| 2-bromoethyl-tris(ethoxy)-silane | 0.37 |
| Control | 0 |

These results establish a clear pattern of excellent performance and a significant improvement over the compounds of the Leasure references.

What is claimed is:

1. A method for regulating the growth of plants as to facilitate fruit abscission, fruit thinning, and fruit ripening which comprises applying to said plants a growth-regulating amount of a compound of the formula

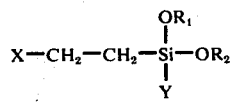

wherein X is chlorine; Y is a group —OR$_3$ and each of R$_1$, R$_2$ and R$_3$ is a group —CO—R$_4$ wherein R$_4$ is an alkyl radical having 1 to 5 carbon atoms.

2. The method of claim 1 in which the abscission of olives, citrus fruits or apples is facilitated.

3. The method of claim 1 in which the ripening of tomatoes is accelerated.

4. The method of claim 1, wherein in said compound R$_4$ is methyl.

5. The method of claim 1, wherein in said compound R$_4$ is ethyl.

6. The method of claim 1, wherein said compound R$_4$ in n-pentyl.

UNITED STATES PATENT AND TRADEMARK OFFICE
CERTIFICATE OF CORRECTION

PATENT NO. : 4,004,909
DATED : January 25, 1977
INVENTOR(S) : Werner Foery, Hans Peter Fischer It is certified that error appears in the above-identified patent and that said Letters Patent are hereby corrected as shown below:

In the heading under Foreign Application Priority Data please add

-- October 6, 1970    Switzerland    14797/70

May 14, 1971    Switzerland    7206/71 --

Signed and Sealed this

Twenty-eighth Day of June 1977

[SEAL]

Attest:

RUTH C. MASON
*Attesting Officer*

C. MARSHALL DANN
*Commissioner of Patents and Trademarks*